US009176102B2

(12) United States Patent
Wang et al.

(10) Patent No.: US 9,176,102 B2
(45) Date of Patent: Nov. 3, 2015

(54) SIMULATION DISTILLATION BY COMPREHENSIVE TWO-DIMENSIONAL GAS CHROMATOGRAPHY

(75) Inventors: Frank C. Wang, Annandale, NJ (US); Bryan E. Hagee, Glassboro, NJ (US)

(73) Assignee: EXXONMOBIL RESEARCH AND ENGINEERING COMPANY, Annandale, NJ (US)

( * ) Notice: Subject to any disclaimer, the term of this patent is extended or adjusted under 35 U.S.C. 154(b) by 716 days.

(21) Appl. No.: 13/021,061

(22) Filed: Feb. 4, 2011

(65) Prior Publication Data

US 2011/0209525 A1    Sep. 1, 2011

Related U.S. Application Data

(60) Provisional application No. 61/338,500, filed on Feb. 19, 2010.

(51) Int. Cl.
| | |
|---|---|
| *G01N 30/78* | (2006.01) |
| *G01N 30/88* | (2006.01) |
| *G01N 31/00* | (2006.01) |
| *G01N 30/46* | (2006.01) |
| G01N 30/02 | (2006.01) |
| G01N 33/28 | (2006.01) |

(52) U.S. Cl.
CPC ............ *G01N 30/463* (2013.01); *G01N 33/287* (2013.01); *G01N 33/2823* (2013.01); *G01N 2030/025* (2013.01); *G01N 2030/8854* (2013.01)

(58) Field of Classification Search
CPC .............................. G01N 30/463; G01N 25/14
USPC ................ 73/23.35, 23.36, 23.38; 702/23, 24
See application file for complete search history.

(56) References Cited

U.S. PATENT DOCUMENTS

| | | | | |
|---|---|---|---|---|
| 4,971,915 | A * | 11/1990 | Schwartz et al. | 436/139 |
| 6,275,775 | B1 * | 8/2001 | Baco et al. | 702/25 |
| 7,447,597 | B2 * | 11/2008 | Wang et al. | 702/32 |
| 7,623,946 | B2 * | 11/2009 | Wang | 700/266 |
| 8,027,792 | B2 * | 9/2011 | Bertoncini et al. | 702/24 |
| 8,177,963 | B2 * | 5/2012 | Greaney et al. | 208/57 |
| 8,301,397 | B2 * | 10/2012 | Bertoncini et al. | 702/25 |
| 2007/0050154 | A1 | 3/2007 | Albahri | |
| 2007/0137481 | A1 | 6/2007 | Blomberg et al. | |
| 2008/0105595 | A1 | 5/2008 | Koseoglu | |
| 2008/0163672 | A1 | 7/2008 | Wang et al. | |
| 2008/0180447 | A1 * | 7/2008 | Bertoncini et al. | 345/440.1 |

(Continued)

OTHER PUBLICATIONS

F. C.-Y. Wang, W. K. Robbins, F. P. Di Sanzo, F. C. McElroy, "Speciation of Sulfur-Containing Compounds in Diesel by Comprehensive Two-Dimensional Gas Chromatography," Journal of Chromatographic Science, vol. 41, Nov./Dec. 2003. pp. 519-523.*

(Continued)

*Primary Examiner* — Lisa Caputo
*Assistant Examiner* — Punam Roy
(74) *Attorney, Agent, or Firm* — Ronald D. Hantman; Glenn T. Barrett; Andrew T. Ward

(57) ABSTRACT

A method to simulate distillation of a petroleum stream by comprehensive two-dimensional gas chromatography including the step of separating said petroleum stream with a two-dimensional gas chromatograph to determine polarity as a function of temperature, and integrating vertically the two-dimensional gas chromatograph at a given temperature to determine signal intensity as a function of temperature.

4 Claims, 4 Drawing Sheets

(56) References Cited

U.S. PATENT DOCUMENTS

2008/0206878 A1* 8/2008 Wang et al. .............. 436/60
2009/0282897 A1 11/2009 Bertoncini et al.

OTHER PUBLICATIONS

Concentration of Solutions, pp. 1-2, Available online on Apr. 13, 2008 at < http://www.chem.purdue.edu/gchelp/howtosolveit/Solutions/concentrations.html>. Accessed onlin on Aug. 29, 2003.*
C. Vendeuvre, R. Ruiz-Guerrero, F. Bertoncini, L. Duval, D. Thiebaul, "Comprehensive Two-Dimensional Gas Chromatography for Detailed Characterisation of Petroleum Products," Oil & Gas Science and Technology-Rev.IFP, vol. 62 (2007), No. 1, pp. 43-55.*
C. Vendeuvre, R. Ruiz-Guerrero, F. Bertoncini, L. Duval, D. Thiebaut, M.-C. Hennion, "Characterisation of middle-distillates by comprehensive two-dimensional gas chromatography (GCxGC): A powerful alternative for performing various standard analysis of middle-distillates," Journal of Chromatography A, 1086 (2005) pp. 21-28.*
J. Blomberg, P. J. Schoenmakers, J. Beens, R. Tijssen, "Comprehensive Two-Dimensional Gas Chromatogrpahy (GCxGC) and Its Applicability to the Characterization Complex (Petrochemcials) Mixtures," J. High Resol. Chromatogr. vol. 20, Oct. 1997. pp. 539-544.*
R. Hua, Y. Li, W. Liu, J. Zheng, H. Wei, J. Wang, X. Lu, H. Kong, G. Xu, "Determination of sulfur-containing compounds in diesel oils by comprehensive two-dimensional gas chromatography with a sulfur chemiluminescence detector," Journal of Chromatography A, 1019 (2003) pp. 101-109.*
J. Beens, U. A. Th. Brinkman, "The role of gas chromatography in compositional analyses in the petroleum industry," Trends in Analytical Chemistry, vol. 19, No. 4, (2000). pp. 260-275.*
Muhlen et al., "Applications of comprehensive two-dimensional gas chromatogrpahy to the characterization of petrochemical and related samples," Journal of Chromatography A, 1105 (2006) 39-50.*
Schoenmakers et al., "comparison of comprehensive two-dimensional gas chromatography and gas chromatography of complex hydrocarbon mictures," Journal of Chromatography A, 892 (2000) 29-46.*
Hua, Ruixiang, et al. "Analysis of sulfur-containing compounds in crude oils by comprehensive two-dimensional gas chromatography with sulfur chemiluminescence detection." Journal of separation science 27.9 (2004): 691-698.*
Roussis, Stilianos G., and W. Patrick Fitzgerald. "Gas chromatographic simulated distillation-mass spectrometry for the determination of the boiling point distributions of crude oils." Analytical chemistry 72.7 (2000): 1400-1409.*
Bradley, Cherlynlavaughn, and Douglas J. Schiller. "Determination of sulfur compound distribution in petroleum by gas chromatography with a flame photometric detector." Analytical chemistry 58.14 (1986): 3017-3021.*
Peaden, Paul A. "Simulated distillation of petroleum and its products by gas and supercritical fluid chromatography: a review." Journal of High Resolution Chromatography 17.4 (1994): 203-211.*
Yan, Xinwei. "Sulfur and nitrogen chemiluminescence detection in gas chromatographic analysis." Journal of Chromatography A 976.1 (2002): 3-10.*
Workman, D. Susan. "Simulated Distillation Measurement." Distillation and Vapor Pressure Measurement in Petroleum Products (2008): 38.*
T. Dutriez, M. Courtiade, D. Thiebaut, H. Dulot and M-C. Hennion, "Improved hydrocarbons analysis of heavy petroleum fractions by high temperature comprehensive two-dimensional gas chromatography", Fuei, 89, pp. 2338-2345. Published online Dec. 16, 2009.
R. Ruiz-Guerrero, C. Vendeuvre, D. Thiebaut, F. Bertoncini and D. Espinat, "Comparison of Comprehensive Two-Dimensional Gas Chromatography Coupled with Sulfur-Chemiluminescence Detector to Standard Methods for Speciation of Sulfur-Containing Compounds in Middle Distillates", Journal of Chromatoaraphic Science, vol. 44, Oct. 2006, pp. 556-573.

* cited by examiner

SIMULATION DISTILLATION BY COMPREHENSIVE TWO-DIMENSIONAL GAS CHROMATOGRAPHY

This application claims the benefit of U.S. Provisional Application No. 61/338,500 filed on Feb. 19, 2010.

BACKGROUND OF THE INVENTION

The present invention relates to the characterization of a petroleum or refinery stream.

Since distillation is a fundamental separation process for the petroleum refining industry, it is essential to be able to characterize a crude oil or refinery stream based on its boiling behavior in the refinery units. Lab scale distillations are relatively slow and costly. Thus, simulated distillation by gas chromatography (GC) has been widely used in the petroleum industry to predict boiling yield. It is an important tool to provide information for parameter setting of the distillation process during refining.

GC Simulated Distillation as practiced in prior art uses a non-polar column (that elutes the molecules based on boiling point) and a flame ionization detector. However, recent developments in GC technology has advanced the separation from conventional one-dimensional (1D) separation (such as boiling point) to comprehensive two-dimensional (2D) separation (such as boiling point and polarity). Comprehensive two-dimensional gas chromatography (2DGC or GC×GC) technique can be applied to simulated distillation. If a hydrocarbon detector such as flame ionization detector (FID) is used, the most significant advantage is that the total yield curve and sub-total yields of each compound class such as saturates, one-ring aromatics, two-ring aromatics, and three aromatics can be determined. If an element-selective detector such as a sulfur chemiluminescence detector (SCD) is used, the sulfur compound classes such as mercaptan/sulfide/thiophene, benzothiophene, and dibenzothiophene) can be determined in additional to the total yield. Likewise a nitrogen specific detector (with 2DGC) could be used to determine the boiling yields of the individual classes of nitrogen containing molecules such as aliphatic amines, pyrrols, indoles, and carbazoles.

SUMMARY OF THE INVENTION

This invention describes a method to perform a simulation of distillation by comprehensive two-dimensional gas chromatography and convert the result to a simulation of distillation with total yield and sub-total yield of pre-defined compound classes as a function of boiling point. The new 2D (2DGC or GC×GC) simulated distillation results will provide more information than traditional 1D simulation distillation results especially in the yield of different compound class. The most direct impact of these results will be in determining the value of the crude oil and/or the refinery streams. This invention could also be of particular value to provide a tool to help the refining industry meet new more restrictive regulations limiting levels of sulfur (and nitrogen) levels in distillate products.

The steps of the present invention characterize a petroleum stream based on its boiling behavior. This method includes the steps of separating the petroleum stream with a two-dimensional gas chromatograph to determine polarity as a function of temperature, and then integrating the two-dimensional gas chromatograph at a given temperature to determine signal intensity.

DETAILED DESCRIPTION OF THE PREFERRED EMBODIMENTS

Experiment Instrumentation and Conditions

The 2D GC (GC×GC) system is peagus 4D manufactured by LECO corp. (St. Jospeh, Mich., USA) consists of an Agilent 6890 gas chromatograph (Agilent Technology, Wilmington, Del.) configured with inlet, columns, and detectors. A split/splitless inlet system with an 100-vial tray autosampler was used. The two-dimensional capillary column system utilizes a non-polar first column (BPX-5, 30 meter, 0.25 mm I.D., 1.0 μm film), and a polar (BPX-50, 3 meter, 0.25 mm I.D., 0.25 μm film), second column. Both capillary columns are the products of SGE Inc. Austin, Tex. A dual jet thermal modulation assembly based on Zoex technology (Zoex Corp. Lincoln, Nebr.) which is liquid nitrogen cooled "trap-release" dual jet thermal modulator is installed between these two columns. A flame ionization detector (FID) and a sulfur chemiluscence detector (SCD) (GE analytical Inc.) are used for the signal detection. A 1.0 microliter sample was injected with 75:1 split at 300° C. from Inlet. Carrier gas is flow at 1.0 ml per minute. The oven was programmed from 60° C. with 0-minute hold and 3° C. per minute increment to 300° C. with 0-minute hold. The total GC run time was 80 minutes. The modulation period was 10 seconds. The sampling rate for the detector was 100 Hz. After data acquisition, it was processed for qualitative and quantitative analysis by the LECO software package that came with the instrument. The display-quality chromatogram was accomplished by converting data to a two-dimensional image that was processed by a commercial program ("Transform" (Research Systems Inc. Boulder, Colo.)). The two-dimensional image was further treated by "PhotoShop" (Adobe System Inc. San Jose, Calif.) to generate publication-ready images.

The simulation distillation conversion was done by exporting the digital data to a Excel file and simulated distillation curves were generated by summing the related Excel cells. The temperature calibration was done by using a normal paraffin mixture to generate the reference retention time under the same experimental conditions.

Example 1

GC×GC or 2DGC-FID chromatogram of a hydrocarbons mixture in the diesel temperature boiling range.

Figure 1:
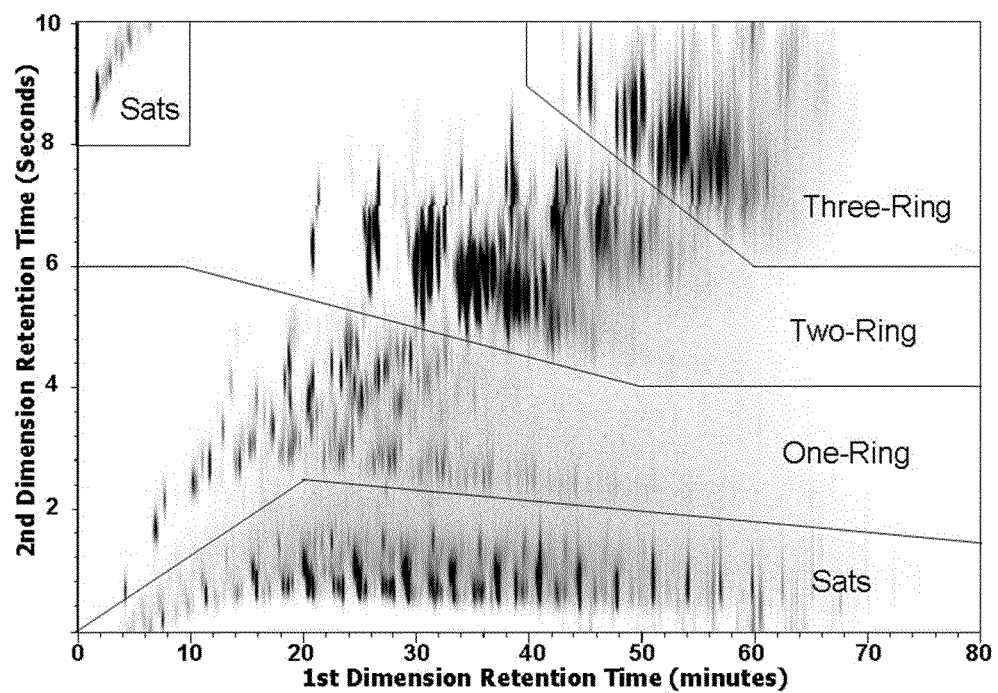
FIG. 1 shows a GC×GC chromatogram of a hydrocarbon mixture in the diesel temperature boiling range.

FIG. 1 shows the GC×GC (or 2DGC) of the hydrocarbon mixture boiling in diesel temperature range. The figure shows separation of saturated hydrocarbons from 1, 2 and 3 ring aromatic hydrocarbons.

Figure 2:
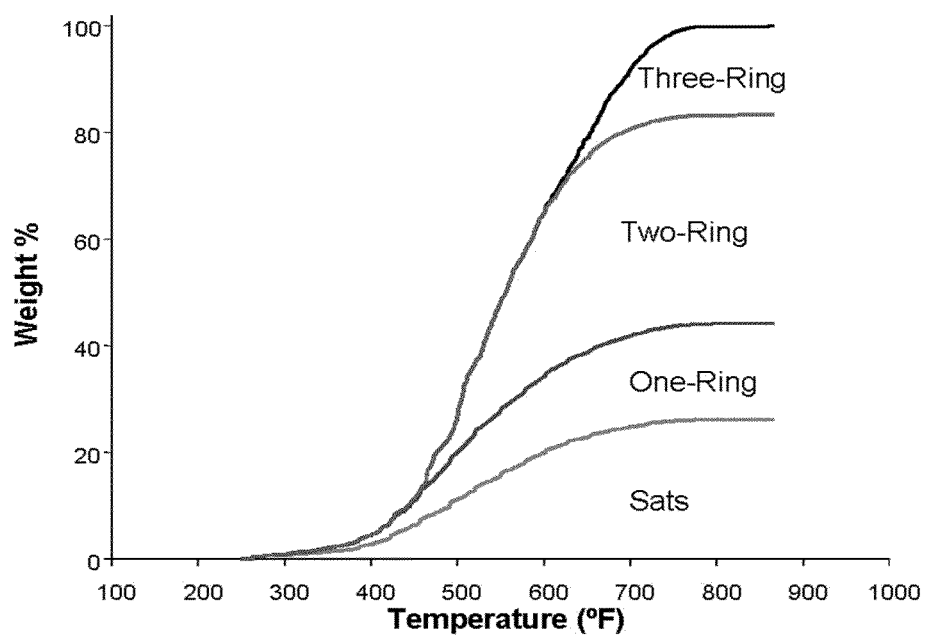
FIG. 2 shows the simulated distillation curve based on the compound class separated in FIG. 1.

The X-axis can be converted from retention time in FIG. 1 to temperature in FIG. 2. The X-axis in FIG. 1 is the first column retention time. As described previously, the first column (of the GC×GC) is a non-polar column. The elution of the non-polar column is based on the boiling point of the compounds. A separated n-paraffin mixture (for example, from n-hexane ($C_6$) to n-Tetracontane ($C_{40}$)) is prepared. This mixture is analyzed with GC×GC at the same condition as running simulated distillation sample. A chromatogram with only n-paraffins will be obtained and each n-paraffin has a unique retention time. Because the boiling point of each n-paraffin is well known, the retention time of each n-paraffin can be exchanged with that specific temperature. The other retention time between each n-paraffin can be interpolated based on the assumption of the linear response of retention time and temperature. With this temperature calibration experiments and interpolation, the X-axis (retention time axis) can be converted to an axis with temperature labeled (a temperature axis).

The flame ionization detector (FID) signal intensity can be converted to weight percentage of sample analyzed. The FID signal intensity is direct proportional to the number of carbon atoms in the component detected. For the hydrocarbon only component, this signal intensity is directly reflected to the relative weight of that specific component. By normalizing the relative signal intensity (relative weight), the signal intensity can be converted to weight percentage (single FID intensity divided by total FID signal intensities in a chromatogram).

The black lines in FIG. 1 divide the region of different compound classes. The GC×GC chromatogram is a display of three dimensional data. All the data along Y-axis can be summarized by compound class region and summed up in each X-axis position. After calibration with the normal paraffin compound mixture, the X-axis retention time can be converted to temperature. The plot of accumulated compound class weight percentage (summarized compound class intensity followed by converting the FID signal intensities to weight percentage) along the temperature scale, the simulated distillation curve can be generated. FIG. 2 is the simulated distillation curve based on the separation of the sample in FIG. 1.

Example 2

If a sulfur chemiluminescence detector (SCD) is attached to a GC×GC (or 2DGC) or integrated with existing flame ionization detector, the breakdown of sulfur species by compound class or type can be determined. Similarly, as described above for the hydrocarbon (FID) detector signal, the sulfur signal from the 2DGC can be used to generate simulated distillation curves for individual sulfur molecular types.

The signal intensity of the sulfur chemiluminescence detector (SCD) can be converted to mole percentage of sample analyzed. The SCD signal intensity is direct proportional to the number of sulfur atoms in the component detected. For the sulfur atom containing hydrocarbons, most of them only have one sulfur atom in each component, this signal intensity is direct reflect to the relative mole of that specific component. By normalize the relative signal intensity (relative mole), the signal intensity can be converted to mole percentage (single SCD intensity divided by total SCD signal intensities in a chromatogram).

Figure 3:
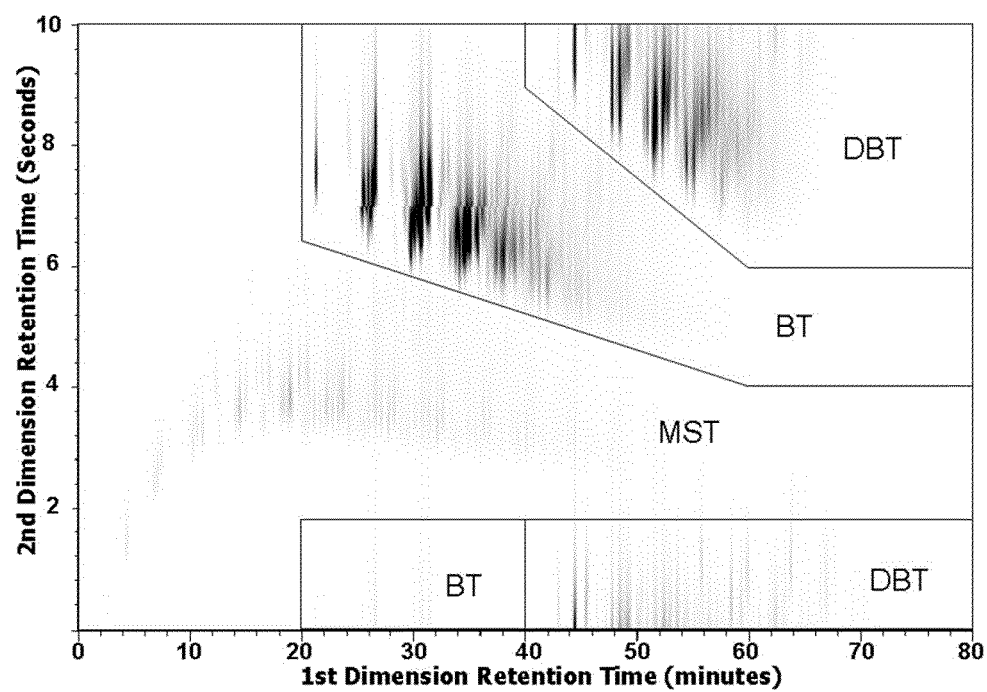
FIG. 3 shows the GC×GC chromatogram of the sulfur containing sample as in FIGS. 1 and 2.

FIG. 3 shows the sulfur containing compound GC×GC (or 2DGC) chromatogram of the same sample as in FIGS. 1 and 2. The sulfur compound classes in FIG. 3 are labeled as follows: MST=mercaptan/sulfide/thiophene, BT=benzothiophene, and DBT=dibenzothiophene. The plot of accumulated compound class mole percentage along the temperature scale can generate the simulated distillation curve.

Figure 4:
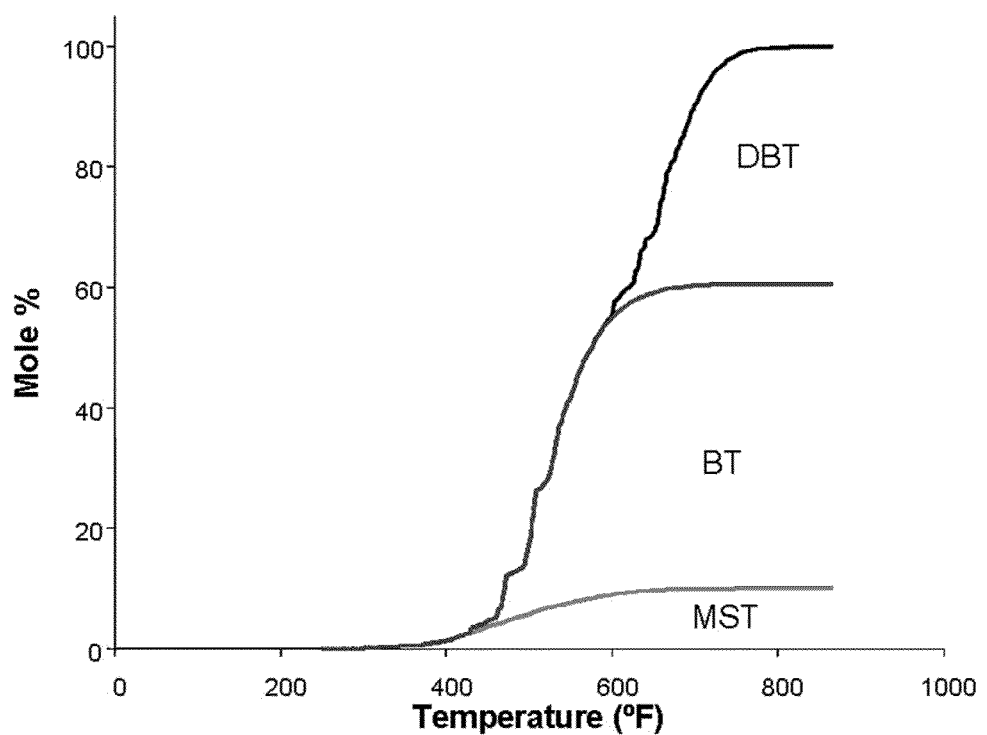
FIG. 4 shows the simulation distillation curve of the sample based on the compound class separated in FIG. 3.

FIG. 4 shows the simulation distillation curve of the sample generated based on the compound class separated in the FIG. 3.

The new 2DGC (or GC×GC) simulated distillation technology will provide more information than traditional 1D simulation distillation result especially in the yield of different compound class. The most direct impact of these results will indicate the value of the crude oil or the refinery streams.

What is claimed is:

1. A method to simulate distillation of a petroleum sample by comprehensive two-dimensional gas chromatography with sub-total yield of compounds in the sample by class as a function of boiling point, comprising:
   a) separating said petroleum stream with a two-dimensional gas chromatograph in a first non-polar dimension of retention time to define component boiling point and a second dimension of polarity with detection of components by polarity class to determine presence of components by relative mole as a function of temperature,
   b) integrating the two-dimensional gas chromatograph at a given temperature to determine the relative molar amount of separated components by class as a function of temperature, wherein said integrating step gives the mole percent of non-carbon elements containing compounds in the sample.

2. The method of claim 1 wherein the non-carbon elements containing compounds include sulfur containing compounds.

3. A method to simulate distillation of a petroleum sample by comprehensive two-dimensional gas chromatography with sub-total yield of compounds in the sample by class as a function of boiling point, comprising:
   a) separating said petroleum stream with a two-dimensional gas chromatograph in a first non-polar dimension of retention time to define component boiling point and a second dimension of polarity with detection of components by polarity class, in which the detection of components by polarity class is carried out using a sulfur chemiluminescence detector, to determine presence of components by relative mole as a function of temperature,
   b) integrating the two-dimensional gas chromatograph at a given temperature to determine the relative molar amount of separated components by class as a function of temperature, wherein said integrating step gives the mole percent of sulfur containing compounds in the sample.

4. A method to simulate distillation of a petroleum sample by comprehensive two-dimensional gas chromatography with sub-total yield of compounds in the sample by class as a function of boiling point, comprising:
   a) separating said petroleum stream with a two-dimensional gas chromatograph in a first non-polar dimension of retention time to define component boiling point and a second dimension of polarity with detection of components by polarity class, in which the detection of components by polarity class is carried out using a nitrogen chemiluminescence detector, to determine presence of components by relative mole as a function of temperature,
   b) integrating the two-dimensional-gas chromatograph at a given temperature to determine the relative molar amount of separated components by class as a function of temperature, wherein said integrating step gives the mole percent of nitrogen containing compounds in the sample.

* * * * *